US006672306B2

United States Patent
Löser et al.

(10) Patent No.: US 6,672,306 B2
(45) Date of Patent: Jan. 6, 2004

(54) ARRANGEMENT FOR SUPPLYING A MEDICAL APPARATUS WITH ANESTHETIC

(75) Inventors: Ralf-Ernst Löser, Lübeck (DE); Michael Rehfeldt, Lübeck (DE)

(73) Assignee: Dräger Medical AG & Co. KGaA, Lübeck (DE)

( * ) Notice: Subject to any disclaimer, the term of this patent is extended or adjusted under 35 U.S.C. 154(b) by 9 days.

(21) Appl. No.: 10/006,706

(22) Filed: Dec. 10, 2001

(65) Prior Publication Data

US 2002/0069876 A1 Jun. 13, 2002

(30) Foreign Application Priority Data

Dec. 9, 2000 (DE) .......................... 100 61 484
Feb. 15, 2001 (DE) .......................... 101 07 005

(51) Int. Cl.[7] .................. A61M 15/00; A61M 16/10
(52) U.S. Cl. .................. 128/203.12; 128/203.13; 128/203.14; 128/203.27
(58) Field of Search .............. 128/202.22, 200.23, 128/203.12, 203.13, 203.14, 203.25, 203.26, 203.27; 222/325, 394, 399

(56) References Cited

U.S. PATENT DOCUMENTS

| 4,611,590 A | * | 9/1986 | Ryschka et al. ....... 128/203.14 |
|---|---|---|---|
| 4,825,860 A | | 5/1989 | Falb et al. |
| 5,168,867 A | * | 12/1992 | Falb et al. ............. 128/203.14 |
| 5,242,403 A | * | 9/1993 | Falb et al. ................. 604/113 |
| 5,243,973 A | * | 9/1993 | Falb et al. ............. 128/203.27 |
| 5,335,652 A | * | 8/1994 | Falb et al. ............. 128/203.14 |
| 5,381,836 A | * | 1/1995 | Braatz et al. ................. 141/21 |
| 5,427,145 A | * | 6/1995 | Grabenkort .............. 137/616.7 |
| 5,478,506 A | * | 12/1995 | Lavimodiere .............. 261/72.1 |
| 5,505,236 A | * | 4/1996 | Grabenkort et al. ........ 141/329 |
| 5,537,992 A | * | 7/1996 | Bjoernstijerna et al. ...................... 128/203.14 |
| 5,585,045 A | * | 12/1996 | Heinonen et al. .......... 261/72.1 |
| 5,682,874 A | * | 11/1997 | Grabenkort et al. ... 128/200.14 |
| 5,730,119 A | * | 3/1998 | Lekholm ................ 128/200.24 |
| 5,758,640 A | * | 6/1998 | Kamppari et al. ...... 128/202.27 |
| 5,799,711 A | * | 9/1998 | Heinonen et al. ............. 141/18 |
| 5,810,001 A | * | 9/1998 | Genga et al. ........... 128/202.27 |
| 5,824,885 A | * | 10/1998 | Lekholm .................... 75/53.01 |
| 6,125,893 A | * | 10/2000 | Braatz et al. .................. 141/18 |
| 6,138,672 A | * | 10/2000 | Kankkunen ............ 128/203.12 |
| 6,216,690 B1 | * | 4/2001 | Keitel et al. ............ 128/203.12 |
| 6,230,666 B1 | * | 5/2001 | Wallin et al. ............. 122/406.3 |
| 6,260,549 B1 | * | 7/2001 | Sosiak .................... 128/200.23 |
| 6,289,891 B1 | * | 9/2001 | Cewers ................... 128/203.12 |
| 6,374,825 B1 | * | 4/2002 | Wallin et al. ........... 128/203.14 |
| 6,394,087 B1 | * | 5/2002 | Kankkunen et al. ... 128/203.16 |
| 6,443,150 B1 | * | 9/2002 | Pessala et al. .......... 128/203.14 |

OTHER PUBLICATIONS

"A New Anesthesia Delivery System" by J. B. Cooper et al, Anesthesiology 49, 1978, pp. 310 to 318.

* cited by examiner

Primary Examiner—Weilun Lo
Assistant Examiner—Michael Mendoza
(74) Attorney, Agent, or Firm—Walter Ottesen

(57) ABSTRACT

An arrangement for supplying a medical apparatus with anesthetic is so improved that, when changing the anesthetic supply vessel (1), the new anesthetic is made available directly and, when there is a malfunction of an anesthetic metering device (2), an exchange is possible in a simple manner. The arrangement includes a supply vessel (1) for the liquid anesthetic (6), a metering device (2) for liquid anesthetic and a pin-and-socket connection (15) between the metering component (2) and a vessel receptacle (3) of a medical apparatus (4). The metering component (2) is electrically drivable and is connected to the supply vessel (1) so as to form a modular unit.

14 Claims, 1 Drawing Sheet

ARRANGEMENT FOR SUPPLYING A MEDICAL APPARATUS WITH ANESTHETIC

BACKGROUND OF THE INVENTION

An arrangement for supplying an anesthetic dispensing apparatus with a liquid anesthetic is disclosed in U.S. Pat. No. 4,825,860. A modularly configured supply vessel for liquid anesthetic is connected to the anesthetic dispensing device of an anesthetic apparatus in that the supply vessel is inserted into the anesthetic dispensing device along a guide. The supply vessel is provided with an identifier which makes it possible for the user to determine which anesthetic is supplied to the anesthetic apparatus from the supply vessel utilized. Furthermore, a fill device, which is specific to the anesthetic, and a fill level indicator are located on the supply vessel. In the coupled state of the supply vessel, the anesthetic reaches the anesthetic dispensing device via a check valve and a tapping stub. The tapping stub is part of the anesthetic dispensing device and, when coupling in, opens the check valve located in the supply vessel so that the anesthetic can flow into the anesthetic dispensing device. A metering device for the anesthetic is located within the anesthetic dispensing device, for example, in the form of a metering pump with which the desired quantity of anesthetic is made available.

It is disadvantageous in this known arrangement that, when changing the anesthetic, the previous anesthetic is still metered for a certain time because it is still located in the connecting line between the tapping stub and the metering device; whereas, the anesthetic, which is next to be applied, is available only after the residual quantity is consumed.

In the article of J. B. Cooper et al entitled "A New Anesthesia Delivery System", Anesthesiology 49, pages 310 to 318 (1978), an anesthetic system is known wherein liquid anesthetic is metered by means of a metering valve from an exchangeable supply vessel into the breathing loop of an anesthetic apparatus. The supply vessel is seated in a socket connection of the anesthetic apparatus and is connected thereby to the metering valve. When changing the anesthetic, the supply vessel disposed in the apparatus is removed by means of a lifting device and is exchanged for another.

In this known system, it is disadvantageous that residual quantities of the previous anesthetic remain in the apparatus when changing the anesthetic. Furthermore, when the metering valve malfunctions, no metering of anesthetic is possible because the metering valve is mounted fixedly on the anesthetic apparatus.

SUMMARY OF THE INVENTION

It is an object of the invention to improve an arrangement of the kind described above so that, when changing the anesthetic, the new anesthetic is directly available for metering and that an exchange is possible in a simple manner when there is a malfunction of the metering valve.

The arrangement of the invention is for supplying a medical apparatus with an anesthetic. The arrangement includes: a supply vessel for holding the anesthetic in liquid form; a metering device for metering the anesthetic and the metering device being connected to the supply vessel so as to form a module therewith; a receptacle on the apparatus for receiving and accommodating the supply vessel; and, a connector between the metering device and the receptacle.

The advantage of the invention is essentially that the metering device and the supply vessel are connected to each other in a module because of the arrangement of the metering device directly on the supply vessel and, in this way, the metering device is exchanged along with the supply vessel when exchanging the latter. The metering device executes a blocking function for the supply vessel as well as a metering function for the anesthetic located in the supply vessel. For this reason, only the anesthetic, which is located in the connected supply vessel, is outputted without this leading to a mixing of the liquid anesthetic when changing the supply vessel. When there is a defect of the metering device, it is a further advantage that only a new supply vessel must be seated in the anesthetic apparatus without a significant interruption of the operation of the apparatus. Maintenance of the metering device is also significantly simplified by the attachment in accordance with the invention because the metering device is freely accessible from all sides and, therefore, maintenance measures can be executed simply and rapidly.

A further advantage of the arrangement according to the invention is that a check valve is mounted on the supply vessel because the interface to the anesthetic apparatus is located behind the metering device and, in this way, the metering device can realize the blocking function in addition to the metering function.

Coupling of the supply vessel to the vessel receptacle of the anesthetic apparatus takes place via a connecting element. The connecting element is either connected to the output of the metering valve so that the anesthetic reaches the anesthetic apparatus directly via the connecting element or it is located on the supply vessel in the region of the anesthetic outputted via the metering valve. The inclusion of the supply vessel in the connecting element affords the advantage that a larger surface is available for the adaptation and, in this way, the connecting element has greater mechanical stability. This is so because the connecting element must be designed for the inherent weight force of the anesthetic volume stored in the supply vessel in the context of strength and tightness characteristics. In addition, possible bending and torsion torques apply. With a connecting element configured in this manner, the supply vessel can be coupled especially simply to the respiratory gas conducting parts of the anesthetic apparatus so that the anesthetic, which is outputted by the metering device, can be mixed directly with the respiratory gas flow. The connecting element can also include a combination of the supply vessel and the metering device so that, at the output of the metering device, the mechanical adaptation is undertaken via the supply vessel in that the supply vessel surrounds the output of the metering device in the form of a sleeve.

According to a feature of the invention, a storage volume is connected downstream of the metering device and the connecting element is located downstream of the storage volume.

In a practical manner, the supply vessel includes a pressurized gas connection via which the interior space of the supply vessel can be charged with a defined pressure. In this way, a defined prepressure is generated for the metering device, for example, for an injection valve. A venting of the supply vessel is also possible via the pressurized gas connection. The arrangement according to the invention is especially advantageous in combination with the metering of anesthetics having a low boiling point because an adequate prepressure can be adjusted for the metering because of the vapor pressure of the anesthetic. A pressure buildup in the supply vessel can be generated by warming the anesthetic with a heater.

In a practical manner, the metering component is attached at the lowest point of the supply vessel so that the entire anesthetic disposed in the supply vessel can be withdrawn. This positioning is suitable for the metering of liquid anesthetic.

The metering component is disposed above the maximum anesthetic fill level in order to make a saturated anesthetic vapor available.

In an advantageous manner, the metering component is configured as a metering valve in the form of an injection valve as known from motor vehicle technology. A large variation of metered anesthetic quantity is realized by controlling the injection valve via a pulse-pause modulated control signal. The injection valve receives electrical control signals from a central control unit with which the injection valve is opened or closed. As an alternative to an injection valve, a micrometering pump can also be utilized.

Pneumatically controlled metering valves can be used as an alternative to electrically operated valves.

The connection is advantageously provided as a pin-and-socket connector, for example, in the form of a rapid connector, as is known from connections for fluid lines. In this way, the part of the connector which is connected to the supply vessel can comprise a hollow elongated body; whereas, a bore configured therefor can be provided on the vessel receptacle as a coupling receptacle. The connector can also be configured as a peripherally extending sealing surface between the supply vessel and the vessel receptacle. The metered anesthetic is outputted to the vessel receptacle in a region enclosed by the sealing surface.

An advantageous use of a supply vessel for liquid anesthetic configured as an insert module comprises connecting this supply vessel with a metering device as a modular unit in order to supply anesthetic to a medical apparatus in correspondence to a metering input.

BRIEF DESCRIPTION OF THE DRAWINGS

The invention will now be described with respect to the single FIGURE of the drawing (FIG. 1) which shows, in schematic section, an arrangement for supplying a medical apparatus with anesthetic.

DESCRIPTION OF THE PREFERRED EMBODIMENTS OF THE INVENTION

Figure 1:
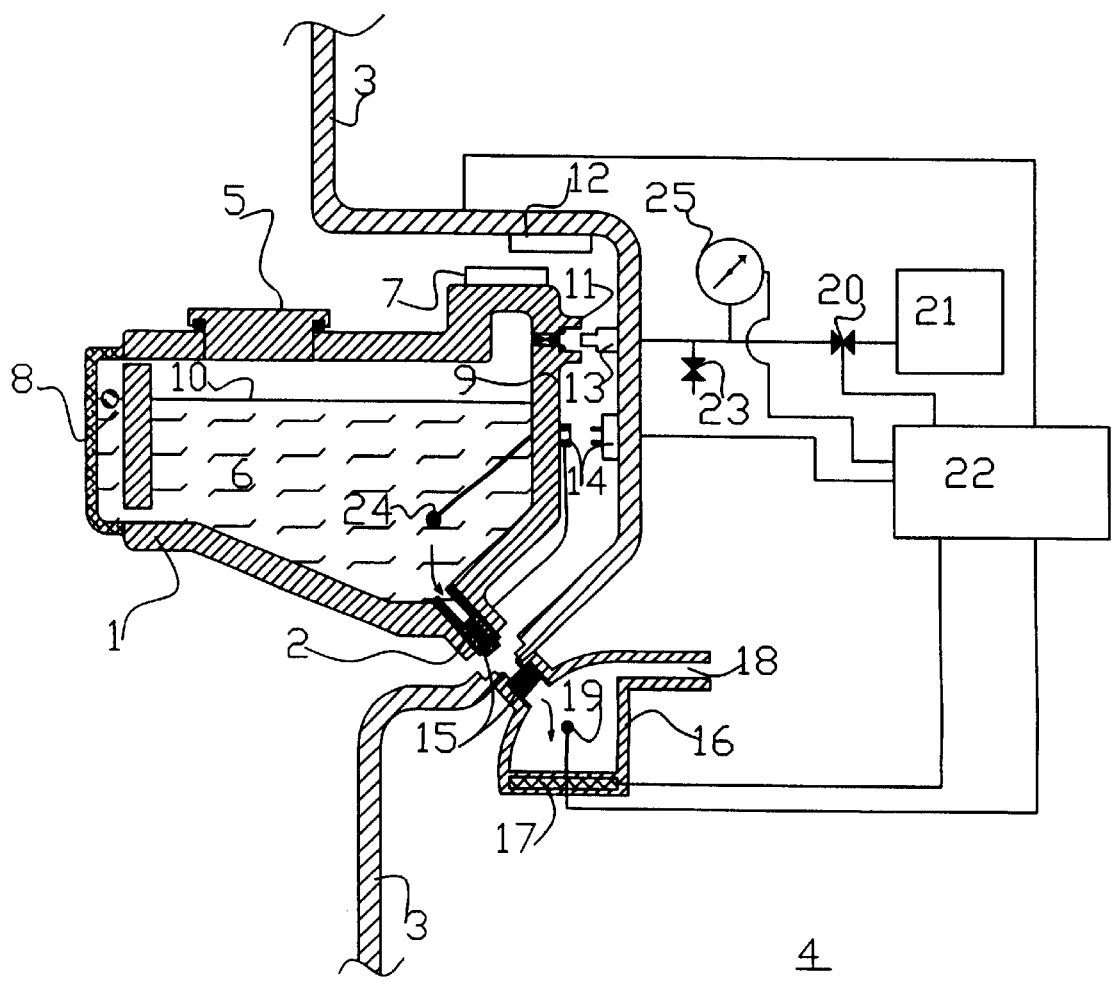

In FIG. 1, a supply vessel 1 is shown schematically in longitudinal section and includes an injection valve 2 on a vessel receptacle 3 of an anesthetic apparatus 4. A fill device 5 for liquid anesthetic and an identifier 7 are provided on the upper end of the supply vessel 1. The fill device 5 and the identifier 7 are assigned to the anesthetic 6 disposed in the supply vessel 1. The fill device 5 is configured for a specific anesthetic so that only anesthetic 6, which corresponds to the identifier 7 can be filled in. The volume of the anesthetic 6 disposed in the supply vessel 1 can be read off on a fill level indicator 8. The injection valve 2 is mounted at the lowest location of the supply vessel 1 so that the anesthetic 6 can be completely removed from the supply vessel 1. A pressurized gas connector 11 is disposed on the back end 9 of the supply vessel 1 above the maximum fill level 10 of the anesthetic. The inner space of the supply vessel 1 can be charged with a predetermined pressure utilizing the pressurized gas connector 11 so that a defined prepressure is present ahead of the injection valve 2 which is necessary for metering the liquid.

The following are arranged on the vessel receptacle 3 of the anesthetic apparatus 4: a reading device 12 for the identifier 7, a pressurized gas stub 13 for the pressurized gas connection 11, an electric connector 14 for the injection valve and a pin-and-socket connector 15 with which a flow connection is established between the output of the injection valve 2 and the vaporization chamber 16 within the anesthetic apparatus 4. The vaporization chamber 16 is heated by a heater 17 to a temperature of approximately 40° C. so that the anesthetic 6 is completely vaporized and can be supplied via a line 18 as a saturated anesthetic vapor into a respirating system (not shown). The temperature in the vaporizing chamber 16 is detected with a temperature sensor 19.

The pressurized gas stub 13 is connected via an electrically drivable pressure controller 20 to a pressurized gas reservoir 21. The supply vessel 1 can be vented as may be required via a venting valve 23 when, for example, the supply vessel must be refilled with anesthetic 6.

The pressure controller 20, the injection valve 2, the heater 17 and the temperature sensor 19 are all connected to a central control unit 22 from which all control commands are outputted for the metering of anesthetic and wherein measured quantities are processed. In this way, the pressure controller 20 receives the input from the control unit 22 for the pressure to be adjusted within the supply vessel 1 and the injection valve 2 receives pulsewidth-modulated control signals via the electric connector 14 for the quantity of anesthetic to be metered.

The temperature sensor 19 measures the temperature within the vaporizing chamber 16. The amount of heat supplied by the heater 17 is adapted by the control unit 22 based on the measured temperature so that a constant temperature of approximately 40° C. is established. Within the supply vessel 1, the temperature of the anesthetic 6 is additionally detected with a temperature sensor 24 which is connected to the control unit 22 via the electric connector 14. A pressure sensor 25 is arranged between the pressurized gas stub and the pressurized gas reservoir 21 and detects the internal pressure within the supply vessel 1. The measured values, which are supplied by the sensors (24, 25), are considered by the control unit 22 for the metering of the quantity of anesthetic.

It is understood that the foregoing description is that of the preferred embodiments of the invention and that various changes and modifications may be made thereto without departing from the spirit and scope of the invention as defined in the appended claims.

What is claimed is:

1. An anesthetic apparatus comprising:

a housing defining a mounting surface;

a chamber mounted in said housing;

a plurality of plug-in supply vessels each holding a particular anesthetic and at least one of said plug-in supply vessels being placed on said mounting surface depending upon need during operational use of said anesthetic apparatus;

each of said plug-in supply vessels including an electric metering device fixedly mounted therein so as to be an integral part of said plug-in supply vessel;

said one plug-in supply vessel and said mounting surface conjointly defining an interface when said one plug-in supply vessel is seated on said mounting surface;

a connector device at said interface for connecting said electric metering device to said housing to facilitate a flow of said anesthetic from said plug-in supply vessel to said chamber;

control means for actuating said electric metering device with a pulse-width modulated control signal to open or close said electric metering device; and, an electric connector at said interface for connecting said control means to said electric metering device for conducting said pulse-width modulated control signal to said electric metering device.

2. The anesthetic apparatus of claim 1, wherein each one of said supply vessels has an interior space for holding the liquid anesthetic; and, each one of said supply vessels has a pressurized-gas connection for charging said interior space with pressurized gas.

3. The anesthetic apparatus of claim 1, wherein each one of said supply vessels has a coding for identifying the anesthetic disposed therein.

4. The anesthetic apparatus of claim 1, wherein said supply vessel has a lowest point and said electric metering device is mounted at said lowest point.

5. The anesthetic apparatus of claim 1, wherein a gaseous anesthetic can be present above said anesthetic in a liquid form in said supply vessel and said electric metering device is mounted in said one supply vessel above the level of said anesthetic in liquid form for metering the gaseous anesthetic.

6. The anesthetic apparatus of claim 1, wherein said electric metering device is configured as an injection valve or micropump.

7. The anesthetic apparatus of claim 6, wherein said injection valve is electrically or pneumatically actuated.

8. The anesthetic apparatus of claim 1, wherein said supply vessel has a fill device for liquid anesthetic specific for a particular liquid anesthetic.

9. The anesthetic apparatus of claim 1, wherein said anesthetic is a liquid and said supply vessel includes a fill level indicator for the liquid anesthetic.

10. The anesthetic apparatus of claim 1, further comprising a temperature sensor for detecting the temperature of said anesthetic in said supply vessel.

11. The anesthetic apparatus of claim 1, wherein each of said supply vessels has an interior space for holding said anesthetic; and, said anesthetic apparatus further comprising a pressure sensor for detecting the pressure present in said interior space.

12. The anesthetic apparatus of claim 1, wherein said connector device is configured as a pin-and-socket connector.

13. The anesthetic apparatus of claim 1, further comprising a storage volume between said electric metering device and said connector device.

14. A plug-in supply vessel unit for use with a medical apparatus when connected thereto, the plug-in supply vessel comprising:

a vessel for holding an anesthetic;

an electric metering device fixedly mounted in said vessel so as to be an integral part thereof;

said electric metering device being configured to respond to a pulse-width modulated control signal to meter said anesthetic to the medical apparatus in a controlled manner when plugged into the medical apparatus;

a connector device for connecting said electric metering device to the medical apparatus to facilitate a flow of said anesthetic from said plug-in supply vessel when said plug-in supply vessel is plugged into the medical apparatus; and, an electric connector element mounted in said supply vessel for conducting said pulse-width modulated control signal to said electric metering device when said plug-in supply vessel is plugged into said medical apparatus.

* * * * *